United States Patent
Joeken et al.

(10) Patent No.: US 6,315,735 B1
(45) Date of Patent: Nov. 13, 2001

(54) DEVICES FOR IN-VIVO DETERMINATION OF THE COMPLIANCE FUNCTION AND THE SYSTEMIC BLOOD FLOW OF A LIVING BEING

(75) Inventors: Stephan Joeken; Matthias Fähle; Ulrich J. Pfeiffer, all of Munich (DE)

(73) Assignee: Pulsion Medical Systems AG (DE)

( * ) Notice: Subject to any disclaimer, the term of this patent is extended or adjusted under 35 U.S.C. 154(b) by 0 days.

(21) Appl. No.: 09/497,195

(22) Filed: Feb. 3, 2000

Related U.S. Application Data

(63) Continuation-in-part of application No. 09/282,421, filed on Mar. 31, 1999, now abandoned.

(51) Int. Cl.[7] .................................................. A61B 5/00
(52) U.S. Cl. ........................ 600/500; 600/504; 600/526
(58) Field of Search ................................. 600/500, 505, 600/504, 485, 526

(56) References Cited

U.S. PATENT DOCUMENTS

| | | | |
|---|---|---|---|
| 5,152,297 | * 10/1992 | Meister et al. | 600/495 |
| 5,183,051 | 2/1993 | Kraidin et al. . | |
| 5,211,177 | 5/1993 | Chesney et al. . | |
| 5,241,966 | 9/1993 | Finkelstein et al. . | |
| 5,316,004 | 5/1994 | Chesney et al. . | |
| 5,400,793 | 3/1995 | Wesseling . | |
| 5,447,163 | * 9/1995 | Apple | 600/500 |
| 5,526,817 | 6/1996 | Pfeiffer et al. . | |
| 5,535,753 | 7/1996 | Petrucelli et al. . | |
| 5,647,369 | 7/1997 | Petrucelli et al. . | |
| 6,017,313 | * 1/2000 | Bratelli et al. | 600/485 |

OTHER PUBLICATIONS

John B. Bedotto, MD, Richard W. Lee, MD, Laryenth D. Lancaster, MD, Marcey Olajos, BS, Steven Goldman, MD, "Cocaine and Cardiovascular Function in Dogs: Effects on Heart and Peripheral Circulation", JJAC vol. 11, No. 6, Jun. 1998, pp. 1337–1342.

Stergiopulos N et al.: "The Four–Element Windkessel Model" Proceedings of the 18th Annual International Conference of the IEEE Engineering in Medicine and Biology Society, "Bridging Disciplines for Biomedicine" (Cat. No. 96CH36036), Proceedings of 18th Annual International Conference of the IEEE Engineering I, pp. 1715–1716 vol 4, XP002155959 1997, New York, NY.

(List continued on next page.)

Primary Examiner—Robert L. Nasser
(74) Attorney, Agent, or Firm—Donald R. Studebaker; Nixon Peabody LLP

(57) ABSTRACT

A device for individual in-vivo determination of the compliance function $C(p)=dV/dp$ of the vascular system downstream of a ventricle and/or systemic blood flow of a living being from the blood pressure $p(t)$ and a reference cardiac output COref. The device comprises a) a pressure sensor which continuously determines the pressure $p(t)$ in the aorta or in the vicinity of the aorta;

b) a computer which
   b1) calculates the mean blood pressure MAP from the blood pressure $p(t)$,
   b2) calculates the systemic resistance R of the body as $$R = \frac{MAP - CVP}{COref},$$

CVP being an arbitrary central venous pressure which is ascertained or estimated, and COref being a reference value for the cardiac output,
   b3) takes at least the first differential of the blood pressure with respect to time $\dot{p}(t)=dp/dt$, and
   b4) calculates the compliance function $C(p)$ at least from $p(t)$, $\dot{p}(t)$ and R using a nonlinear model.

59 Claims, 4 Drawing Sheets

OTHER PUBLICATIONS

Feske W et al.: "Vascular Compliance After Nitroprusside in Hypertension", Proceedings of the Fourteenth Annual Northeast Bioengineering Conference (IEEE Cat. No. 88–Ch2666–6), Durham, NH, Mar. 10–11, 1988, pp. 277–280.

Cappello A et al.: "Analysis of the Arterial Pressure–vol. Curve in the Three—Elementwindkessel Model" Proceedings of the Computers in Cardiology Conference, US, Los Alamitos, IEEE Comp. Soc. Press, Sep. 5, 1993, pp. 385–388.

J.K.J. Li et al.: "A Nonlinear Model of the Arterial System Incorporating a Pressure Dependent Compliance" IEEE Transactions on Biomedical Engineering, vol. 37, No. 7, Jul. 1990, pp. 673–678.

* cited by examiner

DEVICES FOR IN-VIVO DETERMINATION OF THE COMPLIANCE FUNCTION AND THE SYSTEMIC BLOOD FLOW OF A LIVING BEING this application is a Continuation-In-part application of U.S. application Ser. No. 09/282,421 filed Mar. 31, 1999 now abandoned.

BACKGROUND OF THE INVENTION (i) Field of the Invention

The invention relates to a device for individual in-vivo determination of the compliance function $C()=dV/dp$ of the vascular system downstream of a ventricle of a living being from the blood pressure $p(t)$ and a reference cardiac output COref.

The invention also relates to a device for continuously determining the systemic blood flow $q(t)$, in which the blood pressure $p(t)$ in the aorta or in the vicinity of the aorta is determined continuously.

(ii) Description of Related Art

Methods and devices of the type mentioned above are known. In the past, a plurality of methods have been developed with the purpose of calculating the cardiac output (CO) from the arterial blood pressure. On the one hand, methods are proposed in which the CO is determined from a few characteristic values such as, for example, mean arterial pressure (MP), systolic and diastolic pressure (APsys, APdia), ejection time (ET) and patient data (age, sex, weight, height) [4,6,7], and on the other hand algorithms are used in which the complete contour of the pulsating blood pressure curve is utilized to calculate the cardiac output [1,5,20]. In the latter methods, which are also referred to as pulse contour analysis, two different approaches have so far been adopted. Firstly, the CO has been calculated directly from the arterial blood pressure with the aid of some correction factors [19,20] while in other work [5,25] a blood flow is calculated from the pressure, together with particular assumptions, and is assumed to correspond to the actual blood flow in the aorta and therefore to be usable for determining the cardiac output.

The classical Windkessel model, which was first proposed by Hales [26] and has been used by Frank [27] to determine the stroke volume (SV) and, together with the heart rate, the cardiac output, uses only the peripheral resistance R and the compliance C for modeling the cardiovascular system in question. In this model, the arterial blood flow is described by $q(t)$, which can be calculated for given C and R with the aid of the blood pressure $p(t)$ which is to be measured. However, closer examination shows that this simple model reproduces the physiological conditions only incompletely, with the result that many modifications to the original model have been proposed; for an overview reference may be made to [24,28].

The accuracy of these methods depends essentially on how well the assumptions, i.e. the model used, reflect the conditions in the cardiovascular system in question, and in [5] a nonlinear Windkessel model is thus used whose parameters are dictated by the age and sex of the patient. More recent investigations [21] show, however, that the model used in [5] does not reproduce the correct underlying physiological conditions; in particular the compliance (extensibility) of the vessels cannot always be described by the compliance/pressure relationship given in [5]. There may be several causes for this discrepancy. First, only a dependence of the in-vitro determined aortic cross section on the blood pressure is taken into account in [5] and a length variation, as described in [22,23] is neglected; also, only the density of the blood and not the strongly hematocrit-dependent viscosity is taken into account, and the compliance of the peripheral system is likewise ignored. Secondly, apart from age and sex, the compliance function $C(p)$ of a particular individual cannot be used in the method described in [5]. However, it is precisely in the examination of pathophysiological cases, e.g. arteriosclerosis, that it cannot be assumed that $C(p)$ varies according to age and sex, so that the basic model describes the physiological conditions only incompletely [25]. Lastly, it has been shown in [24] that it is to be expected that a modified Windkessel model can reproduce underlying physiological conditions more precisely.

However, a common factor in all the models described above is that the model parameters, after they have been determined once, no longer depend on the condition of the cardiovascular system in question. Nevertheless, almost all parameters can change with time, and for example the systemic resistance R can change as a result of medication. Other parameters, including the expandability and length of the aorta, change so greatly with pressure that they actually have to be regarded as variable even within one heartbeat.

The fact that aortic impedance and compliance cannot be assumed to be constant has been shown both in animal experiments [22] and for humans [29]. Primary causes of this are the expandability, length variation and volume variation of the aorta and vessels in proximity to the aorta. The typical variation in the aortic volume V as a function of pressure has been described inter alia in [30]. Since the compliance of the system is given by $$C(p) = \frac{dV}{dP} \qquad (4)$$

and because of the limited volume the compliance must tend toward zero for very high pressures and cannot be constant. Since the change in volume is caused by length and cross-sectional changes in the vessels, there is also a change in the aortic impedance which, according to the Navier-Stokes equation, is determined on the one hand by the cross section and density of the liquid and, on the other hand, by length, viscosity and density of the blood.

Pressure-dependent aortic impedance and compliance have been discussed inter alia in [5,21] and used therein to investigate nonlinear Windkessel models. In [5] it is in particular assumed that $C(p)$ can be established by age and sex of the patient. The impedance $Z(p)$ is also ignored in this approach. What is more, it follows from the results obtained in [21] that the model used in [5] may to some extent conflict with the true physiological situation. One cause of this is that the compliance and aortic impedance are preset. An approach of this type is unsuitable for taking into account the features characteristic of the patient in question. In addition, the method proposed in [5] cannot be applied without modifications to other species. Further, only the typical aortic diameter investigated beforehand in-vitro and the density of the blood are taken into account in [5]. The effect of aortic length variations, and the dynamic behavior of the vessels in proximity to the aorta and the peripheral vessels and the viscosity of the blood are ignored in the modeling of the conditions existing in vivo.

There is consequently not yet any method which, for individual in-vivo determination of the compliance/pressure relationship, employs the measured variables used here.

These disadvantages are to be eliminated by the device of the present invention by determining all model parameters of interest from measurements on the physiological system in question, i.e. human or animal. To this end, in particular, the blood pressure p(t) in the aorta or in proximity to the aorta is to be measured continuously and a reference cardiac output (COref) is to be measured at least one time. With the aid of these values, all the parameters can be established and then used for hemodynamic investigation.

SUMMARY AND OBJECTS OF THE INVENTION

The object of the invention is to provide a device for individual in-vivo determination of the compliance function of a living being, which reproduces physiological conditions as faithfully as possible.

A further object of the invention is to provide a device for continuously determining the systemic blood flow of a patient which has a low degree of invasiveness and describes the actual blood flow at any given time as accurately as possible.

The way in which these objects are achieved is described in the independent patent claims. Advantageous refinements can be found in the dependent patent claims.

According to the invention, a so-called Windkessel model is used whose parameters can be identified with the aid of a reference measurement in vivo. Subsequently, the systemic flow and other hemodynamic parameters are thereby determined. A Windkessel model adapted and modified in this way describes the cardiovascular system of the individual in question more accurately and can therefore be used for likewise more accurate calculation of the systemic flow and hemodynamic parameters derived therefrom. The method can also be applied directly to other species, without the need to determine previously hypothetical characteristics for this. The extra outlay for the newly developed method consists in the fact that, for calculating an individual compliance function, besides the continuous blood pressure measurement, the cardiac output has at least one time to be determined using a different method, e.g. arterial thermodilution.

BRIEF DESCRIPTION OF THE DRAWINGS

The invention will be explained in more detail below with reference to an illustrative embodiment schematically represented in the figures, in which.

DETAILED DESCRIPTION OF THE PREFERRED EMBODIMENT

Figure 1:
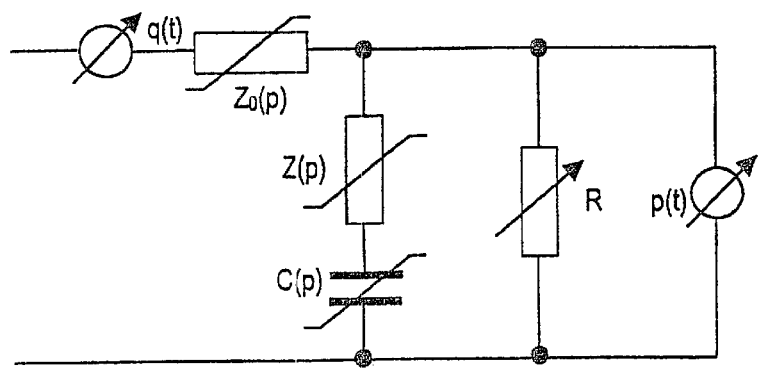
FIG. 1 shows a preferred electrical model circuit for simulating the cardiovascular system in question.
Figure 4:
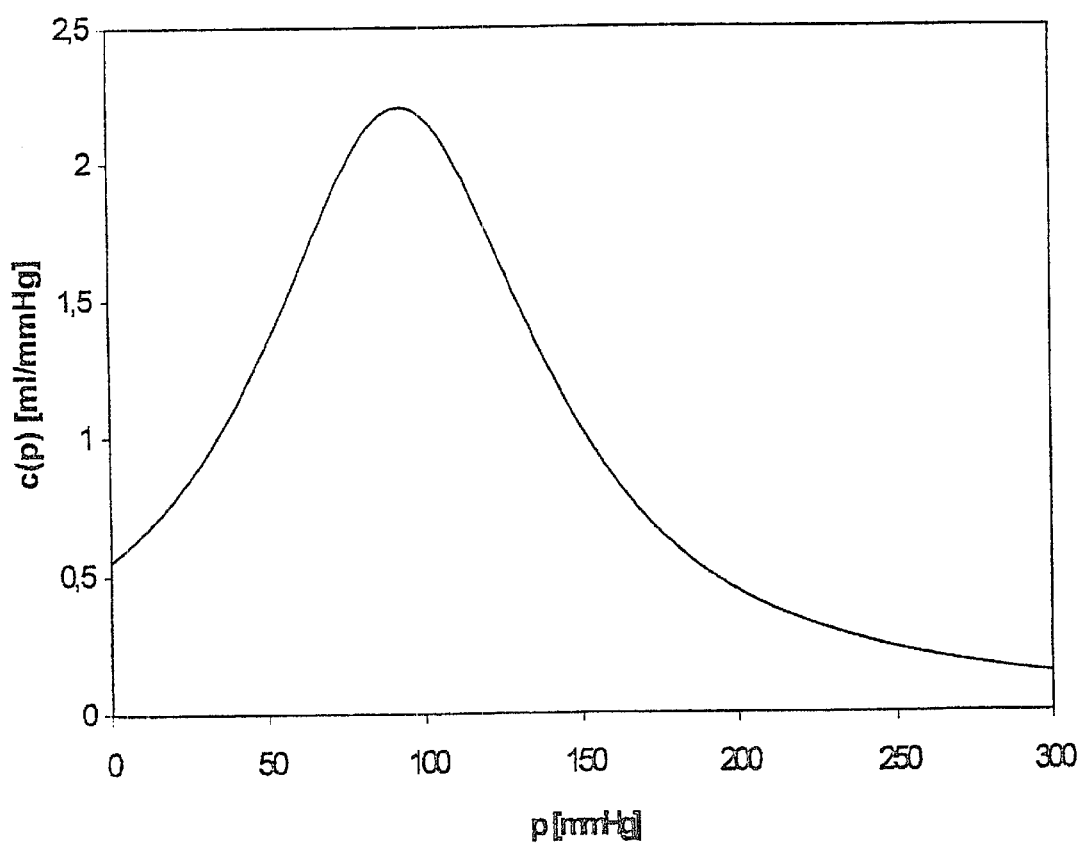
FIG. 4 shows a typical compliance function $C(p)$ of a human aorta.

FIG. 1 shows a nonlinear modified Windkessel model which is preferably used according to the invention, in which the aortic impedance functions $Z(p)$ and $Zo(p)$, the compliance function $C(p)$ and the systemic resistance R are taken into account.

The resistor R in FIG. 1 represents the time-variable peripheral flow resistance of the body. $Zo(p)$ and $Z(p)$ are nonlinear impedances which are dependent on the pressure $p(t)$ and, together with the nonlinear pressure-dependent capacitance $C(p)$, are intended to simulate the behavior of the aorta and the blood vessels in proximity to the aorta.

The result obtained for the model outlined in FIG. 1 with the Fourier transform $$\tilde{p}(\omega) = \int_{-\infty}^{\infty} p(t)\exp(-i\omega t)dt$$

and the function $\tilde{q}(\omega)$, which is to be calculated similarly, for the aortic impedance is $$\lim_{\omega\to\infty} \frac{\tilde{q}(\omega)}{\tilde{p}(\omega)} = \frac{1}{R} + \frac{1}{Z}, \quad (1)$$

so that for R>>Z it follows that $$Z = \lim_{\omega\to\infty} \frac{\tilde{p}(\omega)}{\tilde{q}(\omega)}. \quad (2)$$

The following equation is further satisfied for the compliance C $$C(p) = \frac{q(t) - p(t)/R}{\dot{p}(t) - Z(p)\cdot(\dot{q}(t) - \dot{p}(t)/R)}, \quad (3)$$

in which $\dot{p}(t)=dp(t)/dt$ and $\dot{q}(t)=dq(t)/dt$ are the respective differentials of the pressure and flow with respect to time. Equations (1) to (3) show that C and Z can be calculated for the model in FIG. 1 if the systemic flow $q(t)$, the blood pressure $p(t)$ and the systemic resistance R are known. However, the model describes the cardiovascular system in question well only to the extent that this is possible in the scope of the proposed approach.

Figure 2:
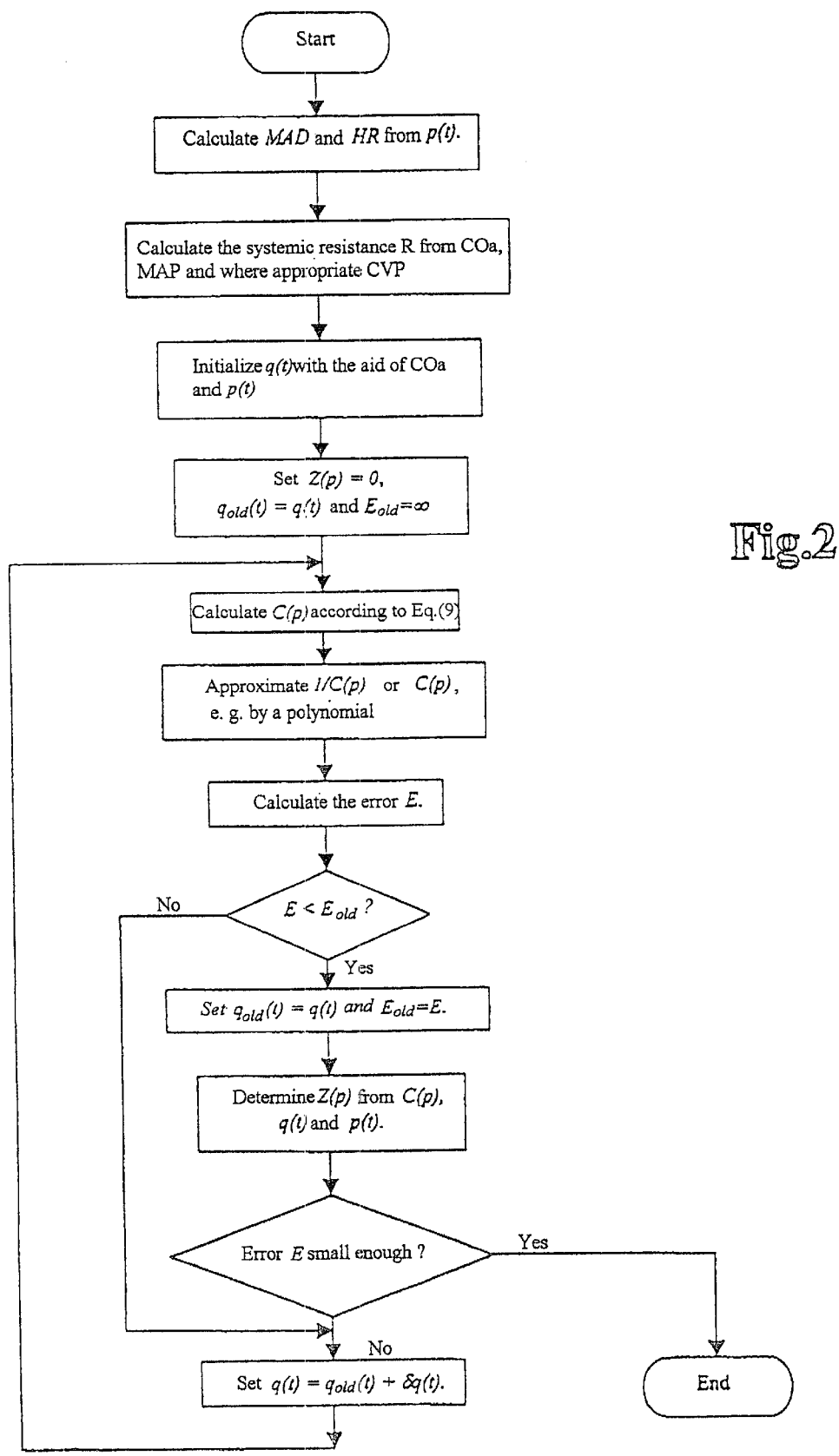
FIG. 2 shows a flow chart for calculating the aortic impedance $Z(p)$, the compliance function $C(p)$ and the blood flow $q(t)$.
Figure 3A:
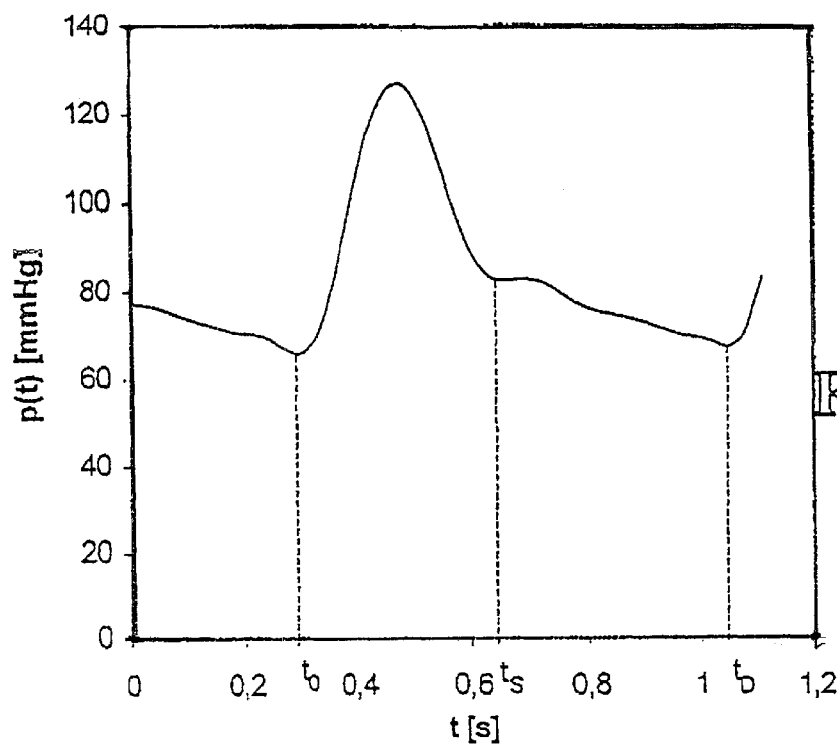
FIG. 3a shows a graph to illustrate the time dependence of the blood pressure $p(t)$, to denoting the time at which the aortic valve opens, ts the time at which the aortic valve shuts and tD the end time of the diastole.
Figure 3B:
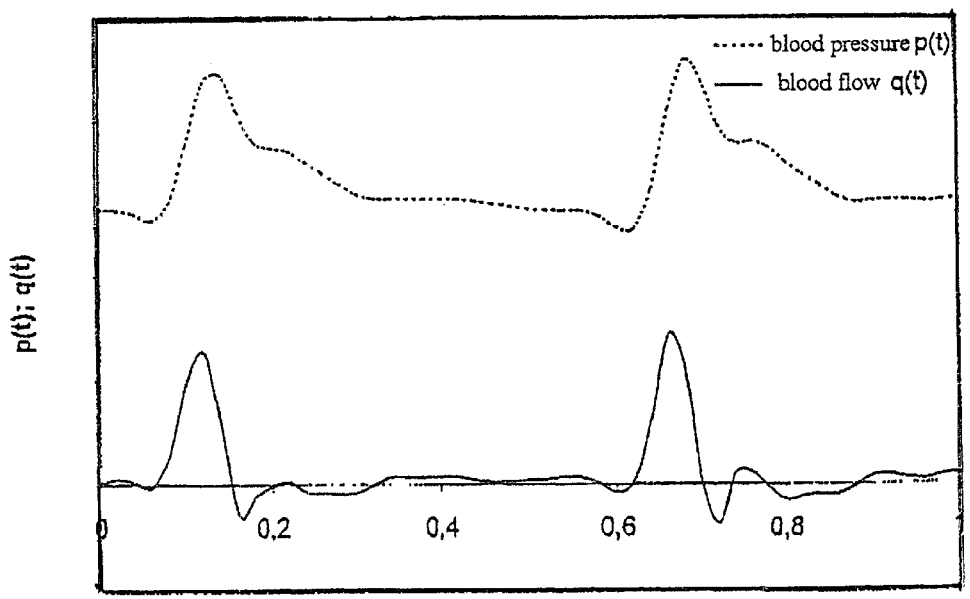
FIG. 3b shows a graph to explain the time dependence of the blood pressure $p(t)$ and the resulting blood flow $q(t)$.

FIG. 2 shows an overview of the refined method.

i) The mean arterial blood pressure MAP and the heart rate HR are firstly determined from the pressure ii) Together with the reference cardiac output COref, which has preferably been determined by arterial thermodilution, and for which the following equation is satisfied $$COref = HR \cdot \int q(t)dt \quad (5)$$

the systemic resistance is calculated according to R=(MAP−CVP)/COref. In this expression, CVP is the central venous pressure which, if it is unknown, can be approximated by a suitable constant pressure, e.g. 0 mmHg.

iii) The next step is to establish a flow $q(t)$, which should be chosen suitably, which is used as the start function in the subsequent iteration and satisfies the underlying physiological conditions. The blood flow $q(t)$ describes the flow which passes directly from the left heart into the aorta. It is therefore required of $q(t)$ that the subconditions the expansion coefficients are determined in such a way that the identity $$q(t) = \frac{p(t)}{R} + \frac{1}{\left[\sum_k \alpha_k p^k\right]} \cdot [\dot{p}(t) \cdot Z(p) \cdot (\dot{q}(t) \cdot p(t)/R)] \quad (11)$$

is optimally satisfied. As a suitable criterion for this, the mean square error $$E = \left\langle \left(q(t) + p(t)/R - [\dot{p}(t) - Z(p)*(\dot{q}(t) - \dot{p}(t)/R)] / \left[\sum_k \alpha_k p^k\right]\right)^2 \right\rangle$$

may be minimized, it being possible to use p(t) and q(t) at all times or alternatively only from preferred time intervals. In this case and below, the notation <·> indicates calculation of the mean.

vii) If E<Eold, then set qold(t)=q(t) and Eold=E and continue with step viii), otherwise go to point x).

viii) Calculate Z(p). On the one hand, the procedure adopted for this may be to determine Z(p) according to equation (1) or (2). In this case, it is assumed that these equations, which are initially valid only for the model in FIG. 1b in which the parameters are not pressure-dependent, also apply for sufficiently short time intervals Δt to the nonlinear approach proposed according to FIG. 1. For the latter, the impedance function can then be ascertained according to equation (2) with $$Z\left(p = \int_{-\Delta t}^{+\Delta t} p(t) dt / 2\Delta t\right)$$

or, equally, by $$Z(p) = \quad (12)$$
$$\sqrt{\left(\int_{t-\Delta t}^{t+\Delta t} p^2(t)dt \cdot \left(\int_{t-\Delta t}^{t+\Delta t} p(t)dt\right)^2\right) / \left(\int_{t-\Delta t}^{t+\Delta t} q^2(t)dt - \left(\int_{t-\Delta t}^{t+\Delta t} q(t)dt\right)^2\right)}$$

even directly from the time-dependent blood pressure p(t) and the blood flow q(t) without a prior Fourier transform.

On the other hand, Z(p) can be calculated yet more simply by $$Z(p) = \frac{A}{\sqrt{C(p)}} \quad (13)$$

as can be seen from the following discussion. The aortic diameter d and length 1 increase with rising pressure, so that to first approximation d 1 may be assumed. According to the Hagen-Poiseuille law, this results in $Z(p) \propto \eta/V$, in which η denotes the viscosity of the blood and V the aortic volume. With C(p)=dV/dp, this gives $C(p) \propto (1/Z)/dp$, from which equation (13) directly follows. The constant of proportionality A which it contains can, for example, be determined by determining the function Z(p) for at least one pressure p according to equation (12).

ix) If the error E is small enough, then the identification of the model parameters is terminated here. Otherwise, it continues with x).

x) The assumed blood flow should finally be varied in such a way that the stroke volume further corresponds to the stroke volume SV=COref/HR which follows from the reference cardiac output. Since, at this time, qold(t) always describes the optimum flow so far, q(t)=qold(t)+δq(t) with ∫δq(t)dt=0 is set.

xi) Continue with step v).

The algorithm indicated in i)–xi) describes the preferred method, in which the reference cardiac output COref and the continuously measured arterial pulse curve p(t) are used to determine all the other values. This guarantees that the compliance function and the aortic impedance function are determined in such a way as is required by the interactions actually taking place in the cardiovascular system in question. In particular, C(p) thereby takes into account not only the variation in the aortic cross section, but also the actual variation in volume of the aorta and peripheral vessels; likewise, a variation in the length of the aorta and the density and curve p(t) and indicates the number of beats per minute. The integration occurring in equations (16) and (17) can in this case be carried out over the entire heartbeat, or alternatively only over the length of the systole, since q(t)=0 is satisfied during the diastole. If the stroke volume SV, and therefore CO as well are calculated during the entire heartbeat, then it is not necessary to determine the end of the systole. To do this (see e.g. [31]), either accurate analysis of the pressure curve would be necessary, in order to determine the position of the so-called dichrotic notch and therefore the end of the systole from p(t), or further measuring instruments such as an ECG would be required. Integration over the entire period is consequently more robust and less involved than those methods which evaluate only a particular period of the heartbeat. If, in addition, the continuously determined cardiac output CO is also calculated from those blood pressure measurements which, together with the reference cardiac volume COref, have been used for model identification using the method described above, then the accuracy of the method for continuous CO calculation can be increased further in that CO=COref must be satisfied and the calibration factor γ is therefore determined according to $$\gamma = \frac{COref}{HR \cdot \int q(t)dt} \quad (19)$$

Figure 5:
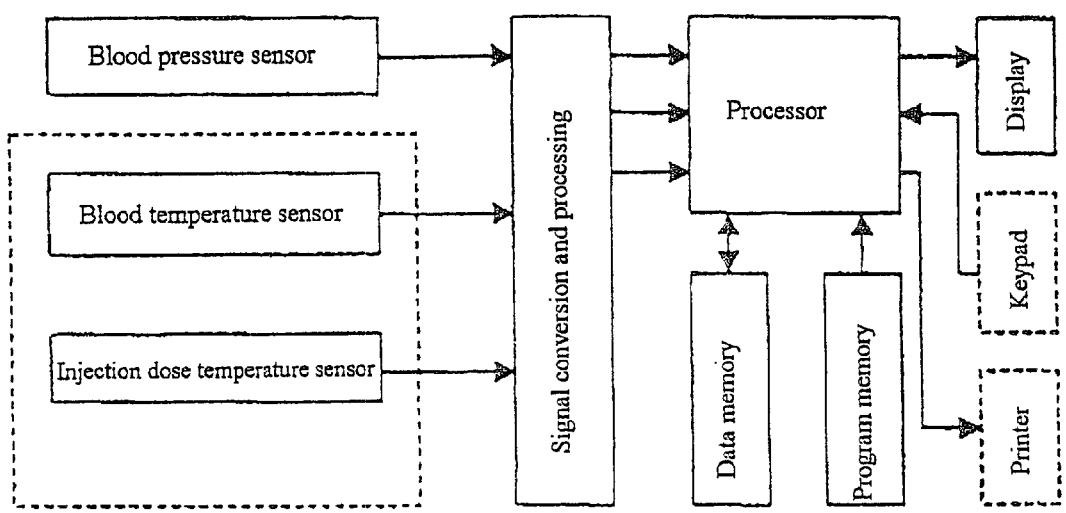
FIG. 5 shows a block circuit diagram of a device according to the invention.

In order to use the described method, it is necessary to have a device whose basic structure is represented in FIG. 5. In this diagram, the components represented by a broken line are optional and at least some of them may be omitted in a minimum configuration of the device. A device of this type consists at least of an evaluation unit, usually a central processing unit, in which the method for determining the individual compliance function C(p) is implemented on its own or together with other methods; in particular, the method for continuously calculating the cardiac output may be employed in the same device. It is also necessary to have a sensor for measuring the blood pressure p(t) in the aorta or in proximity to the aorta and an arrangement for signal processing and signal conversion, a program memory and a data memory, as well as a device for providing the reference cardiac output COref. If COref is determined through arterial thermodilution, then this unit consists at least of a blood temperature sensor and a sensor for measuring the temperature of the injection dose used by this method, see [8]. Since, however, COref can also be obtained in other ways, this module may also have a different form or entry may take place through a keypad which may also be used in the device for the user to enter instructions. There will also be at least one ol the options to have the results of the evaluation displayed, print-ed out or stored on a bulk storage device (not shown).

REFERENCES

[1] U.S: Pat. No. 5,183,051; Kraidin et al.
[2] U.S. Pat. No. 5,211,177; Chesney et al.
[3] U.S. Pat. No. 5,241,966; Finkelstein et al.
[4] U.S. Pat. No. 5,316,004; Chesney et al.
[5] U.S. Pat. No. 5,400,793; Wesseling
[6] U.S. Pat. No. 5,535,753; Petrucelli et al.
[7] U.S. Pat. No. 5,647,369; Petrucelli et al.
[8] U.S. Pat. No. 5,526,817; Pfeiffer et al.
[19] Werner et al. (1953); J. Appl. Physiol. 5:495
[20] Wesseling et al. (1983);
   Adv. cardivasc. Phys. 5:16–52.
[21] Fogliari et al. (1996); Modeling in Physiol. H:2661–2668
[22] Gentile et al. (1988); Cardiovasc. Res. 22:385–389
[23] Wuyts et al. (1995); Phys. Med. Biol. 40:1577–1597
[24] Toy et al. (1985); I7EE Trans. Biomed. Eng. 32(2):174–176
[25] Richter et al. (1984); Biorheology 21:723–734
[26] Hales (1733); Statical Essays: Containing Haemostatics
[27] Frank (1899); Z. Biol. 37:483–526
[28] Yoshigi et al. (1997); Am. J. Physiol. 273 (Heart Circ. Physiol. 42):H19–H27
[29] Langewouters et al. (1984); J. Biomechanics 17:425–435
[30] Hallock et al. (1937); J. Clin. Invest. 16:597
[31] Hoskels et al. (1997); J. Clin. Mon. 13:309–316

What is claimed is:

1. A device for individual in-vivo determination of the compliance function $C(p)=dV/dp$ of the vascular system downstream of a ventricle of a living being from the blood pressure $p(t)$ and a reference cardiac output $CO_{ref}$, comprising:

a) a pressure sensor which continuously determines the pressure $p(t)$ in the aorta or in the vicinity of the aorta;

b) a computer which
   b1) calculates the mean blood pressure MAP from the blood pressure $p(t)$,
   b2) calculates the systemic resistance R of the body as $$R = \frac{MAP - CVP}{CO_{ref}},$$

CVP being an arbitrary central venous pressure which is ascertained or estimated, and $CO_{ref}$ being a reference value for the cardiac output,
   b3) takes at least the first differential of the blood pressure with respect to time $\dot{p}(t)=dp/dt$, and
   b4) calculates the compliance function $C(p)$ at least from $p(t)$, $\dot{p}(t)$ and R using a nonlinear model.

2. The device as claimed in claim 1, wherein the computer only uses values of $p(t)$ which satisfy the following condition for calculating the compliance function $C(p)$:

$$p(t) \leq p(t_s),$$

$t_s$ being the time when the aortic valve shuts.

3. The device as claimed in claim 1 wherein the computer only uses blood pressure values from the diastole for calculating the compliance function $C(p)$.

4. The device as claimed in claim 3 wherein the computer describes the inverse of the compliance function $C(p)$ by a second-order polynomial and approximates $C(p)$ by the following function:

$$C(p) = \frac{MAP^2 CO_{ref}}{\langle \dot{p}(t) \rangle} \cdot \frac{1}{3 \cdot MAP \cdot P - 3 \cdot MAP^2 - P^2}.$$

5. The device as claimed in claim 3, wherein the computer uses the compliance function $C(p)$ calculated for $p(t) \leq p(t_s)$ to expand the blood flow $q(t)$ in terms of a complete function system.

6. The device as claimed in claim 5, wherein the computer describes $q(t)$ in the form of a Fourier series by the following equation $$q(t) = \sum_k q_k \sin\left(k \cdot \pi \cdot \frac{(t - t_o)}{(t_s - t_o)}\right),$$

the coefficients $q_k$ being determined by minimizing the mean square error and the values $t_o$ and $t_s$ denoting the times when the aortic valve is opened and shut.

7. The device as claimed in claim 3, wherein the computer calculates the compliance function $C(p)$ by the following function:

$$C(p) = \frac{CO_{ref} \cdot (P_{notch} - P_{diastole})^2}{\langle dp/dt \rangle} \cdot \frac{1}{3 \cdot (P_{notch} - P_{diastole}) \cdot P - 3 \cdot (P_{notch} - P_{diastole})^2 - P^2}$$

where $P_{notch}$ is the pressure at the dichrotic notch and $P_{diastole}$ is the diastolic pressure.

8. The device as claimed in claim 1 wherein the computer determines a blood flow $q(t)$ on the basis of the pressure $p(t)$ and the first time derivative $dp/dt$, and calculates the compliance function according to $$C(p) = \frac{q(t) - p(t)/R}{\dot{p}(t) - Z(p) \cdot (\dot{q}(t) - \dot{p}(t)/R)}$$

for arbitrary impedance functions $Z(p)$ and arbitrary times $t$ in such a way that $$q(t) = \frac{p(t)}{R} + C(p)[\dot{p}(t) - Z(p) \cdot (\dot{q}(t) - \dot{p}(t)/R)]$$

is optimally satisfied.

9. The device as claimed in claim 1, wherein that computer approximates the inverse of the compliance function, $1/C(p)$, by a finite-order polynomial and uses this polynomial to extrapolate $C(p)$ beyond the pressure range recorded when determining the reference cardiac output.

10. The device as claimed in claim 1, wherein the computer determines the minimum of the function $$E = \left\langle \left( q(t) - \frac{p(t)}{R} - [\dot{p}(t) - Z(p) \cdot (\dot{q}(t) - \dot{p}(t)/R)] \middle/ \left[ \sum_k \alpha_k p^k \right] \right)^2 \right\rangle$$

and then calculates the individual compliance function $C(p)$ as $$C(p) = \frac{1}{\sum_k \alpha_k p^k}.$$

11. The device as claimed in claim 1, wherein the computer approximates the compliance function C(p) by a finite-order polynomial and uses this polynomial to extrapolate C(p) beyond the pressure range recorded when determining the reference cardiac output.

12. The device as claimed in claim 1, wherein the computer varies the assumed blood flow q(t) in such a way as to minimize the mean square error.

13. The device as claimed in claim 1, wherein the computer determines the aortic impedance/pressure relationship by $$Z(P) = \frac{A}{\sqrt{C(p)}}$$

A being a constant of proportionality.

14. The device as claimed claim 1, wherein the computer determines a nonlinear aortic impedance function using the Fourier transforms of the blood pressure $\tilde{p}(\omega)$ and postulated blood flow $\tilde{q}(\omega)$ according to $1/Z = \tilde{q}(\omega \to \infty)/\tilde{p}(\omega \to \infty) - 1/R$ or $Z(p) = \tilde{p}(\omega \to \infty)/\tilde{q}(\omega \to \infty)$.

15. The device as claimed in claim 1, wherein the computer is adapted to determine a blood flow q(t) on the basis of the pressure p(t) and the first time derivative dp/dt and calculate the impedance function $$Z\left(p = \int_{-\Delta t}^{t+\Delta t} p(t)\,dt/2\Delta t\right)$$

according to $$Z(p) = \sqrt{\left(\int_{t-\Delta t}^{t+\Delta t} p^2(t)\,dt \left(\int_{t-\Delta t}^{t+\Delta t} p(t)\,dt\right)^2\right) / \left(\int_{t-\Delta t}^{t+\Delta t} q^2(t)\,dt - \left(\int_{t-\Delta t}^{t+\Delta t} q(t)\,dt\right)^2\right)}.$$

16. The device as claimed in claim 1, wherein the computer approximates the aortic impedance function Z(p) by a finite-order polynomial and uses this polynomial to extrapolate Z(p) beyond the pressure range recorded during calibration.

17. The device as claimed in claim 1, wherein the computer is adapted to calculate the cardiac output continuously together with the heart rate HR from the stroke volume SV according to CO=HR·SV.

18. The device as claimed in claim 17, wherein the computer is adapted to determine the mean pressure MAP continuously from the blood pressure curve and thereby calculate the systemic resistance continuously according to $$R = \frac{MAP - CVP}{CO},$$

for an arbitrary central venous pressure CVP which has been measured or estimated.

19. The device as claimed in claim 17, wherein the computer is adapted to determine the mean pressure MAP continuously from the blood pressure curve and thereby calculate the compliance function continuously according to $$C(p) = \frac{MAP^2 \cdot CO}{\langle \dot{p}(t) \rangle} \cdot \frac{1}{3 \cdot MAP \cdot p - 3 \cdot MAP^2 - p^2}.$$

20. A device for determining cardiovascular parameters of a living being, wherein the device comprises:

a) a pressure sensor which continuously determines the pressure p(t) in the aorta or in the vicinity of the aorta;

b)

b1) means for calculating the mean blood pressure MAP from the blood pressure p(t), b2) means for calculating the systematic resistance R of the body as $$R = \frac{MAP - CVP}{CO_{ref}},$$

CVP being an arbitrary central venous pressure which is ascertained or estimated, and $CO_{ref}$ being a reference value for the cardiac output, b3) means for taking at least the first differential of the blood pressure with respect to time $\dot{p}(t) = dp/dt$, and b4) means for calculating the compliance function C(p) and the blood flow q(t) at least from p(t), $\dot{p}(t)$ and R using a nonlinear model.

21. The device as claimed in claim 20, wherein said means for calculating the blood flow q(t) is adapted to determine the blood flow q(t) by:

$$q(t) = \frac{p(t)}{R} + C(p)[\dot{p}(t) - Z(p) \cdot (\dot{q}(t) - \dot{p}(t)/R].$$

22. The device as claimed in claim 20, wherein the computer uses the compliance function C(p) ascertained according to claim 1.

23. The device as claimed in claim 20 wherein the computer calculates the stroke volume SV by integrating the flow over a suitable period of time in accordance wuth $$SV = \int q(t)dt$$

it being in particular possible for the suitable period of time to correspond to the heartbeat or the ejection time during the heartbeat.

24. The device as claimed in claim 20, wherein the computer calculates the compliance function C(p) by the following function:

$$C(p) = \frac{CO_{ref} \cdot (P_{notch} - P_{diastole})^2}{\langle dp/dt \rangle} \cdot \frac{1}{3 \cdot (P_{notch} - P_{diastole}) \cdot P - 3 \cdot (P_{notch} - P_{diastole})^2 - P^2}.$$

where $P_{notch}$ is the pressure at the dichrotic notch and $P_{diastole}$ is the diastolic pressure.

25. The device as claimed in one of claims 1 and 20, further comprising means for calculating the stroke volume SV, said means for calculating stroke volume adapted to compare the continuous blood flow q(t) with a reference cardiac output $CO_{ref}$, by $$SV = \gamma \int q(t)dt,$$

with $$\gamma = \frac{CO_{ref}}{HR \cdot \int q(t)dt}.$$

26. The device as claimed in one of claims 1 and 20, further comprising means for calculating the stroke volume variation SVV according to $$SVV = \sqrt{\langle SV^2 \rangle - \langle SV \rangle^2},$$

and using the SVV on its own, or with other parameters, e.g. mean blood pressure MAP, systolic pressure APsys, diastolic pressure APDIA and heart rate HR, to correct the stroke volume.

27. A method for individual in-vivo determination of the compliance function C(p)=dV/dp of the vascular system downstream of a ventricle of a living being from the blood pressure p(t) and a reference cardiac output $CO_{ref}$, comprising the setps of:

continuously determining the blood pressure p(t) in the aorta or in the vicinity of the aorta;

calculating the mean blood pressure MAP from the blood pressure p(t) using a computer, calculating the systemic resistance R of the body as $$R = \frac{MAP - CVP}{CO_{ref}},$$

CVP being an arbitrary central venous pressure which is ascertained or estimated, and $CO_{ref}$ being a reference value for the cardiac output using the computer, taking at least the first differential of the blood pressure with respect to time ṗ(t)=dp/dt using the computer, and calculating the compliance function C(p) at least from p(t),ṗ(t) and R using a nonlinear model using the computer.

28. The method as claimed in claim 27, wherein the computer only uses values of p(t) which satisfy the following condition for calculating the compliance function C(p):

$$p(t) \leq p(t_s)$$

$t_s$ being the time when the aortic valve shuts.

29. The method as claimed in claim 27, wherein the computer only uses blood pressure values from the diastole for calculating the compliance function C(p).

30. The method as claimed in claim 29 wherein the computer describes the inverse of the compliance function C(p) by a second-order polynomial and approximates C(p) by the following function:

$$C(p) = \frac{MAP^2 CO_{ref}}{\langle \dot{p}(t) \rangle} \cdot \frac{1}{3 \cdot MAP \cdot P - 3 \cdot MAP^2 - P^2}.$$

31. The method as claimed in claim 29 wherein the computer describes the inverse of the compliance function C(p) by a second-order polynomial and approximates C(p) by the following function:

$$C(p) = \frac{CO_{ref} \cdot (P_{notch} - P_{diastole})^2}{\langle dp/dt \rangle} \cdot \frac{1}{3(P_{notch} - P_{diastole}) \cdot P - 3 \cdot (P_{notch} - P_{diastole})^2 - P^2}.$$

32. The method as claimed in claim 29, wherein the computer uses the compliance function C(p) calculated for p(t)≦p(t,) to expand the blood flow q(t) in terms of a complete function system.

33. The method as claimed in claim 32, wherein the computer describes q(t) in the form of a Fourier series by $$q(t) = \sum_k q_k \sin\left(k \cdot \pi \cdot \frac{(t - t_o)}{t_s - t_o}\right),$$

the coefficients qk being determined by minimizing the mean square error, and the values $t_o$ and $t_s$ denoting the times when the aortic valve is open and shut, respectively.

34. The method as claimed in claim 27, wherein the computer determines a blood flow q(t) on the basis of the pressure p(t) and the first time derivative dp/dt, and calculates the compliance function according to $$C(p) = \frac{q(t) - p(t)/R}{\dot{p}(t) - Z(p) \cdot (\dot{q}(t) - \dot{p}(t)/R)}$$

for arbitrary impedance functions Z(p) and arbitrary times t in such a way that $$q(t) = \frac{p(t)}{R} + C(p)[\dot{p}(t) - Z(p) \cdot (\dot{q}(t) - \dot{p}(t)/R)]$$

is optimally satisfied.

35. The method as claimed in claim 27, wherein the computer approximates the inverse of the compliance function 1/C(p) by a finite-order polynomial and uses this polynomial to extrapolate C(p) beyond the pressure range recorded when determining the reference cardiac output.

36. The device as claimed in claim 27, wherein the computer determines the minimum of the function $$E = \left\langle \left( q(t) - \frac{p(t)}{R} - [\dot{p}(t) - Z(p) \cdot (\dot{q}(t) - \dot{p}(t)/R)] \bigg/ \left[ \sum_k \alpha_k p^k \right] \right)^2 \right\rangle$$

and then calculates the individual compliance function C(p) as $$C(p) = \frac{1}{\sum_k \alpha_k p^k}.$$

37. The method as claimed in claim 27, wherein the computer approximates the compliance function C(p) by a finite-order polynomial and uses this polynomial to extrapolate C(p) beyond the pressure range recorded when determining the reference cardiac output.

38. The method as claimed in claim 27, wherein the computer varies the assumed blood flow q(t) in such a way as to minimize the mean square error.

39. The method as claimed in claim 27, wherein the computer determines the aortic impedance/pressure relationship by $$z(p) = \frac{A}{\sqrt{C(p)}},$$

A being a constant of proportionality.

40. The method as claimed claim 27, wherein the computer determines a nonlinear aortic impedance function using the Fourier transforms of the blood pressure $\tilde{p}(\omega)$ and postulated blood flow $\tilde{q}(\omega)$ according to $1/Z = \tilde{q}(\omega \to \infty)/\tilde{p}(\omega \to \infty) - 1/R$ or $Z(p) = \tilde{p}(\omega \to \infty)/\tilde{q}(\omega \to \infty)$.

41. The method as claimed in claim 27, wherein the computer determines a blood flow $q(t)$ on the basis of the pressure $p(t)$ and the first time derivative $dp/dt$ and calculates the impedance function $$Z\left(p = \int_{-\Delta t}^{+\Delta t} p(t)\, dt / 2\Delta t\right)$$

according to $$Z(p) = \sqrt{\left(\int_{-\Delta t}^{+\Delta t} \dot{p}^2(t)\,dt - \left(\int_{-\Delta t}^{+\Delta t} \dot{p}(t)\,dt\right)^2\right) / \left(\int_{-\Delta t}^{+\Delta t} \dot{q}^2(t)\,dt - \left(\int_{-\Delta t}^{+\Delta t} \dot{q}(t)\,dt\right)^2\right)}.$$

42. The method as claimed claim 27, wherein the computer approximates the aortic impedance function $Z(p)$ by a finite-order polynomial and uses this polynomial to extrapolate $Z(p)$ beyond the pressure range recorded during calibration.

43. The method as in claim 27, wherein said step of determining the reference value for the cardiac output $CO_{ref}$ includes a dilution method.

44. The method as in claim 27, wherein said step of determining the reference value for the cardiac output $CO_{ref}$ includes a thermodilution method.

45. The method as in claim 27, wherein said step of determining the reference value for the cardiac output $CO_{ref}$ includes an arterial thermodilution method.

46. The method as in claim 27, wherein said step of determining the reference value for the cardiac output $CO_{ref}$ includes a dye dilution method.

47. A method for determining cardiovascular parameters of a living being, comprising the steps of:
 continuously determining the pressure $p(t)$ in the aorta or in the vicinity of the aorta,
 calculating the mean blood pressure MAP from the blood pressure $p(t)$ using a computer,
 calculating the systematic resistance R of the body as $$R = \frac{MAP - CVP}{CO_{ref}},$$

CVP being an arbitrary central venous pressure which is ascertained or estimated, and $CO_{ref}$ being a reference value for the cardiac output using the computer,
 taking at least the first differential of the blood pressure with respect to time $\dot{p}(t) = dp/dt$ using the computer, and
calculating the compliance function $C(p)$ and the blood flow $q(t)$ at least from $p(t)$, $\dot{p}(t)$ and R using a nonlinear model using the computer.

48. The method as claimd in claim 47, wherein the computer determines the systemic blood flow $q(t)$ by:

$$q(t) = \frac{p(t)}{R} + C(p)[\dot{p}(t) - Z(p) \cdot (\dot{q}(t) - \dot{p}(t)/R)].$$

49. The method as claimed in claim 47, further comprising the step of calculating a stroke volume SV by integrating the flow over a suitable period of time in accordance with $$SV = \int q(t)\,dt,$$

it being in particular possible for the suitable period of time to correspond to the heartbeat or the ejection time during the heartbeat.

50. The method as claimed in claim 47, further comprising the steps of calculating a stroke volume SV, by comparing the continuous blood flow $q(t)$ with a reference cardiac output $CO_{ref}$ by $$SV = \gamma \int q(t)\,dt \text{ with } \gamma = \frac{CO_{ref}}{HR \cdot \int q(t)\,dt}.$$

51. The method as claimed in claim 47, further comprising the step of calculating the stroke volume variation according to $$SVV = \sqrt{\langle SV^2 \rangle - \langle SV \rangle^2}$$

and using the SVV on its own, or with other parameters, e.g. mean blood pressure MAP, systolic pressure APsys, diastolic pressure APDIA and heart rate HR, to correct the stroke volume.

52. The method as claimed in claim 47, further comprising the step of calculating the cardiac output continuously together with the heart rate HR from the stroke volume SV according to CO=HR·SV.

53. The method as claimed in claim 52, wherein the computer determines the mean pressure MAP is continuously determined from the blood pressure curve and thereby calculates the systemic resistance continuously according to $$R = \frac{MAP - CVP}{CO},$$

for an arbitrary central venous pressure CVP which has been measured or estimated.

54. The method as claimed in claim 52 wherein the computer describes the inverse of the compliance function $C(p)$ by a second-order polynomial and approximates $C(p)$ by the following function:

$$C(p) = \frac{MAP^2 CO_{ref}}{\langle \dot{p}(t) \rangle} \cdot \frac{1}{3 \cdot MAP \cdot P - 3 \cdot MAP^2 - P^2}.$$

55. The method as claimed in claim 52, wherein the mean pressure MAP is continuously determined from the blood pressure curve and thereby calculates the compliance function continuously according to $$C(p) = \frac{CO_{ref} \cdot (P_{notch} - P_{diastole})^2}{\langle dp/dt \rangle} \cdot \frac{1}{3(P_{notch} - P_{diastole}) \cdot P - 3 \cdot (P_{notch} - P_{diastole})^2 - P^2},$$

where $P_{notch}$ is the pressure at the dichrotic notch and $P_{diastole}$ is the diastolic pressure.

56. The method as in claim 47, wherein said step of determining the reference value for the cardiac output $CO_{ref}$ includes a dilution method.

57. The method as in claim 47, wherein said step of determining the reference value for the cardiac output $CO_{ref}$ includes a thermodilution method.

58. The method as in claim 47, wherein said step of determining the reference value for the cardiac output $CO_{ref}$ includes an arterial thermodilution method.

59. The method as in claim 47, wherein said step of determining the reference value for the cardiac output $CO_{ref}$ includes a dye dilution method.

* * * * *